(12) United States Patent
Seo et al.

(10) Patent No.: US 7,550,157 B2
(45) Date of Patent: Jun. 23, 2009

(54) METHOD FOR THE PREPARATION OF POLYMERIC MICELLE VIA PHASE SEPARATION OF BLOCK COPOLYMER

(75) Inventors: Min-Hyo Seo, Daejeon (KR); Yil-Woong Yi, Daejeon (KR); Jae-Won Yu, Daejeon (KR)

(73) Assignee: Samyang Corporation, Seoul (KR)

( * ) Notice: Subject to any disclaimer, the term of this patent is extended or adjusted under 35 U.S.C. 154(b) by 579 days.

(21) Appl. No.: 10/276,352

(22) PCT Filed: May 11, 2001

(86) PCT No.: PCT/KR01/00765

§ 371 (c)(1),
(2), (4) Date: Nov. 12, 2002

(87) PCT Pub. No.: WO01/85216

PCT Pub. Date: Nov. 15, 2001

(65) Prior Publication Data

US 2003/0180363 A1 Sep. 25, 2003

(51) Int. Cl.
*A61K 9/50* (2006.01)
(52) U.S. Cl. .................. 424/490; 424/450; 424/400; 424/489
(58) Field of Classification Search .................. None
See application file for complete search history.

(56) References Cited

U.S. PATENT DOCUMENTS

| 5,449,513 | A | | 9/1995 | Yokoyama et al. |
| 5,510,103 | A | | 4/1996 | Yokoyama et al. |
| 5,663,168 | A | * | 9/1997 | Rosel et al. ............. 514/227.5 |
| 5,683,723 | A | | 11/1997 | Spenlehauer et al. |
| 5,702,717 | A | | 12/1997 | Cha et al. |
| 5,877,205 | A | | 3/1999 | Andersson |
| 5,922,754 | A | | 7/1999 | Burchett |

FOREIGN PATENT DOCUMENTS

EP 0645145 B1 12/1997

OTHER PUBLICATIONS

Hawley's Condensed Chemical Dictonary, 14 ed. 2002 "Solvent" and "Organic Chemistry" disclosures. Dowloaded from the World Wide Web on Jul. 11, 2006.*
Materials Safety Data Sheet for Polyethylene Glycol 400 Mar. 6, 2004.*
Aliabadi et al, "Micelles of methoxy poly(ethylene oxide)-b-poly(eta-caprolactone) as vehicles for the solubilization ond controlled delivery of cyclosporine A" Journal of Controlled Release 104(2005) 301-311.*
Szebeni et al "Complement activation by cremophor EL as a possible contributer to hypersensitivity to paclitaxel: an in vitro study" Journal of the National Cancer Institute vol. 90, 4, Feb. 18, 1998.*
Kessel, D. "Properties of Cremophor EL Micelles Probed by Fluorescence" Photochemistry and Photobiology, vol. 56 No. 4, pp. 447-451, 1992.*
Montazeri et al., Micelles of methoxy poly(ethylene oxide)-b-poly(e-caprolactone) as vehicles for the solubilization and controlled delivery of cyclosporine A. J. Controlled Release 104 (2005) 301-311.*
K. Kataoka, Design of nanoscopic vehicles for drug targeting based on micellization of amphiphilic block copolymers, J. Macromol. Sci.-Pure Appl. Chem A31 (1994) 1759-1769.
H. Maeda, The tumor blood vessel as an ideal target for macromolecular anticancer agents, J. Control. Rel. 19(1992) 315-324.
Marie-Christine Jones, Jean-Christophe Leroux, Polymeric micelles—a new generation of colloidal drug carriers, European Journal of Pharmaceuticals and Biopharmaceutics 48 (1999) 101-111.
Xichen Zhang, John K. Jackon, Helen M. Burt, Development of amphiphilic diblock copolymers as micellar carriers of taxol, International Journal of Pharmaceutics 132 (1996) 195-206.
G .Kwon, et al., Block copolymer micelles for drug delivery: loading and release of doxorubicin, J. Contr. Rel. 48 (1997) 195-201.
G. Kwon, et al., Physical entrapment of Adriamycin in AB block copolymer micelles, Pharm. Res. 12 (1995) 92-195.
So Yeon Kim, et al, Methoxy poly(ethylene glycol) and ϵ-caprolactone amphiphilic block copolymric micell containing indomethacin. II. Micelle formation and drug release behaviours.
Marie-Christine Jones, Jean-Christophe Leroux, Polymeric micelles—a new generation of colloidal drug carriers, European Journal of Pharmaceuticals and Biopharmaceutics 48 (1999) 101-111.
Xichen Zhang, John K. Jackon, Helen M. Burt, Development of amphiphilic diblock copolymers as micellar carriers of taxol, International Journal of Pharmaceutics 132 (1996) 195-206.
G .Kwon, et al., Block copolymer micelles for drug delivery: loading and release of doxorubicin, J. Contr. Rel. 48 (1997).
G. Kwon, et al., Physical entrapment of Adriamycin in AB block copolymer micelles, Pharm. Res. 12 (1995) 92-195.
So Yeon Kim, et al, Methoxy poly(ethylene glycol) and ϵ-caprolactone amphiphilic block copolymric micell containing indomethacin. II. Micelle formation and drug release behaviours.
Marie-Christine Jones, Jean-Christophe Leroux, Polymeric micelles - a new generation of colloidal drug carriers, European Journal of Pharmaceuticals and Biopharmaceutics 48 (1999) 101-111.
Xichen Zhang, John K. Jackon, Helen M. Burt, Development of amphiphilic diblock copolymers as micellar carriers of taxol, International Journal of Pharmaceutics 132 (1996) 195-206.

* cited by examiner

*Primary Examiner*—Michael G. Hartley
*Assistant Examiner*—Eric E Silverman
(74) *Attorney, Agent, or Firm*—Thorpe North & Western LLP

(57) ABSTRACT

A method for preparing a biodegradable polymeric micellar composition using liquid polyethylene glycol as a phase separation medium. The present invention also provides an efficient method to effectively incorporate a hydrophobic drug into a polymeric micelle in a polyethylene glycol separating medium.

8 Claims, No Drawings

METHOD FOR THE PREPARATION OF POLYMERIC MICELLE VIA PHASE SEPARATION OF BLOCK COPOLYMER

This application is based on PCT /KR01/00765, which claims priority, based on a Korean patent application No. 2000-25256 filed on May 12, 2000.

BACKGROUND OF THE INVENTION

1. Field of the Invention

The present invention provides a method for preparation polymeric micelles and use thereof in pharmaceutical applications. The micelle, which is used as a carrier for hydrophobic drugs, is prepared via phase separation of a biodegradable polymeric composition containing a block copolymer having a hydrophilic poly(alkylene glycol) component and a hydrophobic biodegradable polymer component suspended in a poly(ethylene glycol) medium.

2. Related Art

Many important drugs are hydrophobic and have limited solubility in water. In order to attain the expected therapeutic effect from such drugs, it is usually required that a solubilized form of the drug be administered to a patient. Therefore, solubilization of a poorly water soluble drug is key technology in the preparation of a formulation for oral or parenteral, especially intravenous, administration of the drug. Common methods used for solubilization of poorly water soluble drugs are: i) dissolving the drug in a co-solvent of a water-miscible organic solvent and water; ii) modifying the drug to its salt form which is soluble in water; iii) forming a soluble drug-complex using a complexing agent; and iv) micellizing the drug in an aqueous medium with a surfactant. Leon Lachman, "The Theory and Practice of Industrial Pharmacy", Lea & Febiger, Philadelphia, 1986.

Solubilization methods using surfactants, not requiring any changes in the chemical structure of a drug, have been widely used to solubilize various drugs. Non-ionic surfactants, e.g. polyoxyethylene sorbitan fatty acid esters (Tween®) and polyoxyethylene alkyl ethers(Brij™ or Myrj™), are commonly used as the surface active agents. European Patent EP 0645145 discloses a method of solubilizing a typical poorly water soluble drug, paclitaxel, by use of Cremophor EL™, a polyoxyethylene castor oil derivative. However, the use of these surfactants, is restricted due to toxic side effects such as hypersensitivity. They have limitations in that their poor ability to stabilize micelles can cause precipitation of the drug when the micellar solution is either stored or is to remain in place for an extended period of time.

Polymeric micelles have been recently investigated as potential carriers for hydrophobic drugs. Eur. J. Pharm. Biopharm. 48(1999) 101-111. Polymeric micelles are characterized by a core-shell structure consisting of hydrophobic inner core and hydrophilic outer shell. A poorly water soluble drug is entrapped within the hydrophobic core of the micelle. There are two typical methods of entrapping a poorly water soluble drug in the hydrophobic core of a micelle: a) a block copolymer and a poorly water soluble drug are dissolved in a water-miscible organic solvent, such as ethanol or N,N-dimethyl formamide(DMF), and the solution is dialyzed in water (Dialysis Method); and b) a drug solution of a water-immiscible organic solvent, such as dichloromethane or chloroform, is added to an aqueous polymeric solution and the organic solvent is evaporated from the solution mixture (O/W Emulsion-Solvent Evaporation Method).

Yokoyama et al. discloses methods of incorporating a poorly water soluble drug into the inner core of a polymeric micelle using an A-B type diblock copolymer composed of a hydrophilic methoxypolyethylene glycol block(A) and a hydrophobic polyamino acid(B). See U.S. Pat. Nos. 5,510,103 and 5,449,513. According to those patents, an aqueous micellar solution of the diblock copolymer and an organic solvent solution of the hydrophobic component are prepared in separate containers. The two solutions are then mixed and simply stirred, heated or sonicated to incorporate the hydrophobic drug into the polymeric micelles. The aqueous polymer solution and the drug solution in DMF are mixed together and the mixture is dialyzed against an excess of water. These methods require preparing an aqueous micellar solution prior to incorporating a drug into the polymeric micelle. See also, G. Kwon, et al., Block copolymer micelles for drug delivery: loading and release of doxorubicin, J. Contr. Rel. 48(1997) 195~201; G. Kwon, et al., Physical entrapment of Adriamycin in AB block copolymer micelles, Pharm. Res. 12(1995) 192~195.

X. Zhang et al. reported that a polymeric micelle prepared with a diblock copolymer of poly(lactic acid) and monomethoxy poly(ethylene glycol) was useful as a carrier of paclitaxel. X. Zhang et al., Int. J. Pharm. 132(1996) 195-206. Shin et al. disclose a solubilization method for indomethacin using a diblock copolymer of poly(ethylene glycol) and polycaprolactone. I. Gyun Shin et al., J. Contr. Rel., 51(1998) 13-22. In these methods, a poorly water soluble drug is incorporated in a polymeric micelle wherein the polymers are biocompatible and biodegradable. According to their methods, a drug and a block copolymer are dissolved together in an organic solvent, especially in a water-miscible organic solvent, such as tetrahydrofuran or dimethyl formamide. The polymeric micelles are prepared by first dialyzing the solution in water and then freeze-drying the aqueous micellar solution. Alternatively, a solution of a polymer and drug in a water-miscible organic solvent, acetonitrile, is prepared. The organic solvent is slowly evaporated to give a homogeneous drug-polymer matrix and the matrix is then dispersed in an aqueous medium at about 60° C. to form the polymeric micelles. It is stated that a polymeric micelle containing the drug cannot be formed if an organic solvent other than an acetonitrile, such as chloroform, dichloromethane, ethyl acetate, acetone, methanol, ethanol, or tetrahydrofuran is used for dissolving the drug and polymer. The aqueous polymeric micellar solutions are prepared by heating, ultrasonic treatment, vortexing or mechanical mixing.

As described above, conventional solubilization methods for poorly water soluble drugs using polymeric micelles employs complicated steps including formation of an aqueous polymeric micellar solution containing a poorly water soluble drug, followed by preparation of a freeze-dried powder. Moreover, the powdered product must then be reconstituted so it is not possible to store the product in an aqueous solution for a prolonged period of time because of the hydrolyzable and biodegradable components in the polymer. Another disadvantage is that this method can not be applied to a polymer having a melting temperature below about 50° C. Furthermore, all existing methods for incorporating a drug into the micelle require using an organic solvent and preparing the polymeric micelles in an aqueous medium. It is very difficult to completely eliminate the organic solvent in the process of preparing a polymeric micelle or incorporating a drug into the micelle. In addition, the remaining organic solvent decreases the stability of the micelle in water and makes it difficult to control the release rate of the drug.

SUMMARY OF THE INVENTION

The present invention discloses a preparation method for preparation of a non-aqueous polymeric micellar system without the use of significant amounts of an organic solvent which may have toxic side effects and require removal by evaporation. The present invention provides a method for preparing a polymeric micellar composition wherein a hydrophobic drug is effectively incorporated, via phase separation of a biodegradable polymeric composition containing a block copolymer having a hydrophilic poly(alkylene glycol) component and a hydrophobic biodegradable polymer component suspended in a poly(ethylene glycol) medium, into the micelle.

The block copolymer is mixed together with a hydrophobic drug in the liquid polyethylene glycol. A solution of the polymer and the drug is then obtained by heating the mixture. The solution is then slowly cooled and polymeric micelles having a core-shell structure form in the solution via phase separation of the block copolymer from the liquid poly(ethylene glycol). The terms poly(ethylene glycol), polyethylene glycol, or PEG, as used herein, are interchangeable and shall also be deemed to include derivatives of PEG unless otherwise specifically stated. Such derivatives will be more specifically described in the disclosure that follows. Since only the hydrophilic component block and not the hydrophobic component block of the copolymer has an affinity or attraction for the poly(ethylene glycol) matrix, the block copolymer forms a core-shell structure wherein the hydrophobic biodegradable polymer block occupies the inner core and the hydrophilic poly(alkylene glycol) block forms the outer shell in the poly(ethylene glycol) medium or carrier.

The present invention uses liquid polyethylene glycol as a medium for mixing and solubilization of a hydrophobic drug and the hydrophilic/hydrophobic copolymer, followed by phase separation of the polymeric micelle which provides for a one step process of preparing the polymeric micelle containing a poorly water soluble drug. In contrast, conventional methods employ two steps: 1) a polymeric micelle is formed in an aqueous media and 2) a poorly water soluble drug is incorporated into the micelle in the aqueous polymer solution.

The present invention also provides a method of incorporating a poorly water soluble drug into a polymeric micelle having a core-shell structure using liquid polyethylene glycol as a phase separation medium, removing the liquid polyethylene glycol and freeze-drying the resulting micellar solution.

If desired, a biocompatible water-miscible organic solvent may be added to the composition of the present invention to facilitate better solubility of the drug. The amount of organic solvent added depends on the solubility of the drug, and the preferred content of the solvent is less than 50 wt % based on the amount of poly(ethylene glycol) or its derivatives.

The present invention further provides an efficient method to effectively incorporate a hydrophobic drug into a polymeric micelle in a polyethylene glycol separating medium. Aqueous solutions of micelles from which the polyethylene glycol has been removed can be filtered to sterilize them, freeze-dried and stored as a stable powder formulation. Furthermore, the composition can easily be reconstituted as a solution and injected into the body and is therefore is useful for the intravenous administration of poorly water soluble drugs.

Additional features and advantages of the invention will be apparent from the detailed description which follows, taken in conjunction with the accompanying examples, which together illustrate, features of the invention.

DETAILED DESCRIPTION

Reference will now be made to the exemplary embodiments and specific language will be used herein to describe the same. It will nevertheless be understood that no limitation of the scope of the invention is thereby intended. Alterations and further modifications of the inventive features illustrated herein, and additional applications of the principles of the invention as illustrated herein, which would occur to one skilled in the relevant art and having possession of this disclosure, are to be considered within the scope of the invention.

The present invention is directed to a method for preparing a polymeric micelle having a core-shell type structure using liquid polyethylene glycol as a phase separation medium and a method of incorporating a poorly water soluble drug into the polymeric micelle. A polymeric micelle composition, in a dry-state, is obtained by dialyzing the polymeric micellar PEG solution, containing a drug or not, against water to remove the PEG followed by freeze-drying the resulting solution.

The composition containing an amphiphilic block copolymer having a hydrophilic poly(alkylene glycol) component and a hydrophobic biodegradable polymer component dispersed or suspended in a poly(ethylene glycol) medium are disclosed in copending PCT/KR00/00885, hereby fully incorporated by reference (which has been filed in the U.S. as Ser. No. 09/807,487). The amphiphilic block copolymer comprises a hydrophilic poly(alkylene glycol) component and a hydrophobic biodegradable polymer component. The polyalkylene glycol suitable as the hydrophilic component in the block copolymer of the present invention is a member selected from the group consisting of polyethylene glycol, monoalkoxy polyethylene glycol, or monoacyloxy polyethylene glycol, wherein the molecular weight of the polyalkylene glycol is preferably within the range of 1,000~20,000 Daltons.

The hydrophobic biodegradable polymer component of the copolymer of the present invention is a member selected from the group consisting of polylactides, polycaprolactone, copolymers of lactide and glycolide, copolymers of lactide and caprolactone, copolymers of lactide and 1,4-dioxan-2-one, polyorthoesters, polyanhydrides, polyphosphazines, poly(amino acid)s and polycarbonates. Preferably, the hydrophobic biodegradable polymer component of the copolymer of the present invention is a member selected from the group consisting of a polylactide, polycaprolactone, a copolymer of lactide and glycolide, a copolymer of lactide and caprolactone, and a copolymer of lactide and 1,4-dioxan-2-one. The molecular weight of the hydrophobic biodegradable polymer component is preferably within the range of 1,000~20,000 Daltons, and more preferably within the range of 1,000~10,000 Daltons.

The amphiphilic block copolymer of the present invention may be an AB type diblock or an ABA or BAB type triblock copolymer comprising a hydrophilic poly(alkylene glycol) A-block component (A) and a hydrophobic biodegradable polymer B-block component(B), which form micelles in an aqueous medium, and are dissolved or mixed homogeneously in a poly(ethylene glycol) medium.

The amphiphilic block copolymers can be prepared according to methods described in U.S. Pat. Nos. 5,683,723 and 5,702,717, hereby fully incorporated by reference. For example they may be prepared via ring opening bulk polymerization of one of the monomers, such as a lactide, caprolactone, 1,4-dioxan-2-one, or a glycolide, with a polyethylene glycol derivative in the presence of stannous octoate as a catalyst. Block copolymers having a poly(amino acid) block are prepared by reaction of an amino acid N-carboxy anhydride with a polyethylene glycol derivative. The hydrophilic polyethylene glycol block is preferably in the range of 30~70% by weight of the block copolymer, and most preferably 40~60% by weight.

The liquid polyethylene glycol used for the phase separation medium in preparing polymeric micelles (containing a poorly water soluble drug) of the present invention is preferably selected from the group consisting of dihydroxy, monoalkoxy, monoacyloxy, dialkoxy, or diacyloxy polyethylene glycol having a molecular weight of 200~20,000 Daltons and a melting temperature of less than 65° C. More preferably, the liquid polyethylene glycol is selected from the group consisting of dihydroxy polyethylene glycol, dialkoxy polyethylene glycol, and diacyloxy polyethylene glycol which are liquid at a temperature of 0~40° C. and has a molecular weight of 200~20,000 Daltons, preferably 200~10,000 Daltons, and most preferably 200~1,000 Daltons. Water, or an aqueous solution, can be added to the liquid polyethylene glycol to facilitate phase separation of the block copolymer micelles. Preferably the amount added will be less than 10% by weight of the liquid polyethylene glycol solution.

A small amount of an organic solvent can be added to facilitate the solubility of a poorly water soluble drug in the liquid polyethylene glycol that is used for the phase separation medium. The solvent should be biocompatible and easily eliminated by evaporation or dialysis. For example, ethanol, acetic acid, or acetone can be used as the solvent. Ethanol or acetic acid is the preferred selection for this purpose. The amount added is preferably 0.1~20% and is most preferably less than 10% by weight of the amount of polyethylene glycol used for the phase separation medium. Such amounts of organic solvents are considered, by definition herein, to be insignificant amounts when compared to the amount polyethylene glycol liquid medium.

Any drug having a water solubility of less than 10 mg/ml can be used as the "hydrophobic drug" or "poorly water soluble drug" to be incorporated in the polymeric micelle of the present invention. Examples of hydrophobic drugs that can be used include anticancer agents, antiinflammatory agents, antifungal agents, antiemetics, antihypertensive agents, sex hormones, and steroids. Typical examples of the hydrophobic drugs are: anticancer agents such as paclitaxel, camptothecin, doxorubicin, daunomycin, cisplatin, 5-fluorouracil, mitomycin, methotrexate, and etoposide; antiinflammatory agents such as indomethacin, ibuprofen, ketoprofen, flubiprofen, dichlofenac, piroxicam, tenoxicam, naproxen, aspirin, and acetaminophen; antifungal agents such as itraconazole, and ketoconazole; sex hormones such as testosterone, estrogen, progestone, and estradiol; steroids such as dexamethasone, prednisolone, and triamcinolone; antihypertensive agents such as captopril, ramipril, terazosin, minoxidil, and parazosin; antiemetics such as ondansetron and granisetron; antifungal agents such as amphotericin, metronidazole, and fusidic acid; cyclosporine; and biphenyl dimethyl dicarboxylic acid. The present invention is particularly useful for administering anti-cancer drugs such as paclitaxel, taxotane, doxorubicin, cisplatin, carboplatin, 5-FU, etoposide, and camptothecin; sex hormones such as testosterone, estrogen, and estradiol; steroids such as triamcinolone acetonide, hydrocortisone, dexamethasone, prednisolone, and betamethasone; cyclosporine; and prostagladins.

According to a preferred embodiment of the present invention, a polymeric micelle is prepared as follows:

1) Dissolving of the amphiphilic block copolymer: The amphiphilic block copolymer is added to liquid polyethylene glycol to form a mixture. The mixture is heated and/or stirred until a solution is obtained.

2) Cooling and/or stirring of said solution, thereby forming a polymeric micelle by phase separation from the liquid polyethylene glycol which serves as a phase separation medium.

3) Dialyzing the polymeric micellar containing composition formed in step (2), in liquid polyethylene glycol against excess water to remove the liquid polyethylene glycol that was used as a phase separation medium.

4) freeze-drying the dialyzed aqueous solution to give a polymeric micellar composition in a fine powder state.

According to the present invention, a polymeric micelle containing a hydrophobic drug is prepared by dissolving the drug together with the amphiphilic block copolymer in the liquid polyethylene glycol in step (1) as described above. At a temperature of 30~100° C., the drug and the amphiphilic block copolymer can be easily dissolved in the liquid polyethylene glycol. If a small amount of organic solvent, such as ethanol or acetic acid, is used to facilitate the solubility of a hydrophobic drug, the solution of step (1) is further slowly stirred at a temperature of 30~100° C. to evaporate the organic solvent before the solution is cooled in step (2). In any case, a drug containing polymeric micelle composition in the state of a fine powder is obtained by dialyzing the polymeric micellar solution against excess water followed by freeze-drying the resulting solution according to steps (3) and (4). Before dialyzing the polymeric micellar containing composition, the polymeric micellar containing solution can be diluted with distilled water to facilitate dialysis.

For the pharmaceutical use of the polymeric micelle prepared by the present invention, the dialyzed composition containing a poorly water soluble drug obtained in step (3), is filtered through a membrane filter having a pore size of 0.22~0.80 μm to sterilize the composition and then freeze-dried in an aseptic environment in step (4). When the block copolymer is dissolved in the liquid polyethylene glycol, the block copolymer content of the combined copolymer/polyethylene glycol composition is preferably 1~50% by weight, and more preferably 10~40% by weight. The poorly water soluble drug content in the polymeric micelle is preferably 0.1~20% by weight based on the total weight of the drug and the block copolymer, and most preferably 1~15% by weight. The stabilizer, such as mannitol, sorbitol, lactose, or sucrose, can be added to increase the stability of the freeze-dried micelle of the present invention. A stabilizer can be added in an amount of 0.1~200% by weight based on the total weight of the drug and the block copolymer. The polymeric micelle prepared according to the present invention has a diameter of 10~500 nm, preferably 10~20 nm, and the micellar composition when dispersed in saline can be used as a carrier for poorly a water soluble drug via various routes: injectable(iv, im, sc); oral; and nasal routes.

While the following examples are provided for the purpose of illustrating certain aspects of the present invention, they are not to be construed as limiting the scope of the appended claims.

EXAMPLES

Example 1

Preparation of a mPEG-PLA Diblock Copolymer 2 g of monomethoxy polyethylene glycol (mPEG with a molecular weight of 2,000 Daltons) was added to a round-bottomed flask and dried at a temperature of 100° C. while under vacuum (0.2 torr). Into the flask was added 2 g of lactide and 0.02 g of stannous octoate(catalyst). This mixture was stirred for 6 hours at 120° C. under nitrogen flow. The reaction product was cooled to room temperature and dissolved in 10 ml of dichloromethane. The solution was then poured into cold anhydrous ether (−10~0° C.) to precipitate the polymers, namely, diblock copolymers of monomethoxy polyethylene glycol and polylactide(mPEG-PLA). The precipitated polymers were dried at 30° C. under vacuum (0.1 mmHg) for 48 hours.

Example 2

Preparation of a mPEG-PLGA Diblock Copolymer (LA/GA=7/3)

A diblock copolymer of monomethoxy polyethylene glycol and poly(lactide-glycolide) (mPEG-PLGA) was prepared by the same method as in Example 1, using 2 g of monomethoxy polyethylene glycol(molecular weight of 2,000 Daltons), 0.7 g of lactide, and 0.3 g of glycolide in the presence of 0.01 g of stannous octoate as a catalyst.

Example 3

Preparation of a mPEG-PLDO Diblcok Copolymer (LA/DO=5/5)

A diblock copolymer of monomethoxy polyethylene glycol and poly(lactide-p-dioxanone) (mPEG-PLDO) was prepared by the same method as in Example 1, using 2 g of monomethoxy polyethylene glycol(molecular weight of 2,000 Daltons), 0.5 g of lactide, and 0.5 g of 1,4-dioxan-2-one in the presence of 0.01 g of stannous octoate as a catalyst.

Example 4

Preparation of a mPEG-PCL Diblock Copolymer

A diblock copolymer of monomethoxy polyethylene glycol and polycaprolactone (mPEG-PCL) was prepared by the same method as in Example 1, using 2 g of monomethoxy polyethylene glycol (molecular weight of 2,000 Daltons), and 0.8 g of caprolactone in the presence of 0.008 g of stannous octoate as a catalyst.

Example 5

Preparation of a mPEG-PLA Diblock Copolymer

A diblock copolymer of monomethoxy polyethylene glycol and polylactide (mPEG-PLA) was prepared by the same method as in Example 1, using 2 g of monomethoxy polyethylene glycol (molecular weight of 5,000 Daltons), and 1.8 g of lactide in the presence of 0.018 g of stannous octoate as a catalyst.

Example 6

Preparation of a Polymeric Micelle of mPEG-PLA (1) Formation of a Polymeric Micelle A 1 g sample of the diblock copolymer prepared in Example 1 (molecular weight: mPEG-PLA=2,000-1,800 Daltons) was mixed with 4 g of liquid polyethylene glycol (Mw: 600 Daltons) and stirred for 30 minutes at 80° C. to obtain a solution. The solution was then slowly cooled to room temperature (25° C.) for 1 hour to obtain a composition of polymeric micelles formed in the liquid polyethylene glycol.

(2) Separation of the Polymeric Micelle

The composition obtained from the above step (1) was diluted with 4 ml of distilled water and the aqueous solution was then put into a dialysis bag. The liquid polyethylene glycol was removed from the solution by dialyzing the solution against water for 12 hours. An aqueous polymeric micellar solution was obtained.

(3) Sterilization and Drying

The dialyzed aqueous micellar solution obtained from the above step (2) was then filtered through a membrane filter, having a pore size of 0.22 μm, to sterilize it and it was then freeze-dried in an aseptic environment.

Comparative Example 1

A Polymeric Micelle of mPEG-PLA

According to a method described in U.S. Pat. No. 5,510,103, a polymeric micellar solution was prepared by dissolving 1 g of the diblock copolymer prepared in Example 1(molecular weight: mPEG-PLA=2,000-1,800 Daltons) in enough distilled water to give a concentration of 0.05% (w/v). The polymeric micellar composition in powder form was obtained by freeze-drying the aqueous micellar solution.

The polymeric micelles prepared in Example 6 and Comparative Example 1 was dispersed in suitable amount of distilled water to give a concentration of 0.1% (w/v) and the particle size of each micellar solution was determined by a dynamic light scattering (DLS) method. The average micelle size of each preparation was nearly the same: 40 nm for Example 6, and 35 nm for Comparative Example 1

Example 7

Preparation of a Polymeric Micelle of mPEG-PLA Containing Paclitaxel (1) Formation of the Polymeric Micelle A mixture was formed by adding 0.9 g of the diblock copolymer prepared in Example 1 (molecular weight: mPEG-PLA=2,000-1,800 Daltons) and 0.1 g of paclitaxel to 2 g of liquid polyethylene glycol (Mw: 600 Daltons). The mixture was stirred at 60~90° C. for 20 minutes to give a clear solution. The solution was slowly cooled to room temperature (about 25° C.) for 1 hour. A polymeric micellar composition containing paclitaxel was obtained by phase separation from the liquid polyethylene glycol.

(2) Separation of the Polymeric Micelle

The composition obtained from the step (1) above was diluted with 2 ml of distilled water and then put into a dialysis bag. The liquid polyethylene glycol was removed from the solution by dialyzing against water for 12 hours, and an aqueous polymeric micellar solution containing paclitaxel was obtained in the dialysis bag.

(3) Sterilization and Drying

The dialyzed aqueous solution obtained from the step (2) above was filtered through a membrane filter, with a pore size of 0.22 μm, to sterilize it, and then freeze-dried in an aseptic environment. The average micelle size was 45 nm, and paclitaxel in the micelle was 9.8% (loading efficiency=98%) by weight based on the total weight of the drug and the block copolymer.

Comparative Example 2

Polymeric Micelles of mPEG-PLA Containing Paclitaxel

A polymeric micellar composition containing paclitaxel was prepared by a method described in U.S. Pat. No. 5,510,103, hereby incorporated by reference.

Step 1: Formation of a Polymeric Micelle

A polymeric micellar solution was prepared by dissolving 0.9 g of the diblock copolymer prepared in Example 1 (molecular weight: mPEG-PLA=2,000-1,800 Daltons) in 900 ml of distilled water to give a concentration of 0.1% (w/v).

Step 2: Incorporation of a Drug

A 0.1 g of paclitaxel dissolved in 1 ml acetone was added into the composition obtained from the Step 1 above. The mixture was stirred for 2 hours at 80° C. and then cooled to room temperature (about 25° C.).

Step 3: Sterilization and Drying

The aqueous solution obtained from Step 2 above was filtered through a membrane filter with a pore size of 0.22 μm, to sterilize it, and was then freeze-dried in an aseptic environment giving a powder state of the polymeric micellar composition.

The polymeric micelles prepared in Example 7 and Comparative Example 2 were dispersed in a suitable amount of distilled water to give a concentration of 0.1% (w/v) and the particle size of each micellar solution was determined by a dynamic light scattering (DLS) method. The average micelle size of each preparation was nearly the same: 55 nm for Example 7, and 50 nm for Comparative Example 2.

The amount of drug incorporated in each composition prepared in Example 7 and Comparative Example 2 was also determined by a HPLC assay. The amount of paclitaxel for the composition of Example 7 was 9.8% (loading efficiency=98%) by weight based on the total weight of the drug and the block copolymer, and 8.7% (loading efficiency=87%) for the composition of Comparative Example 2. The polymeric micellar composition of the present invention exhibited a higher loading efficiency than that prepared according to U.S. Pat. No. 5,510,103.

Example 8

Polymeric Micelles of mPEG-PLDO Containing Cyclosporine A (1) Formation of a Polymeric Micelle A mixture was prepared by adding 0.95 g of the diblock copolymer prepared in Example 3 (molecular weight: mPEG-PLDO=2,000-1,940 Daltons) and 0.05 g of cyclosporine A to a solution mixture consisting of 3.2 g of liquid polyethylene glycol (mw: 600 Daltons) and 0.8 g of ethanol. The mixture was slowly heated to a temperature of 90° C., while stirring, for 30 minutes to give a solution. The solution was slowly cooled to room temperature (about 25° C.) for 1 hour, and a polymeric micellar composition containing cyclosporine A was obtained.

(2) Separation of the Polymeric Micelle

The composition obtained from the step (1) above was diluted with 4 ml of distilled water and then put into a dialysis bag. The liquid polyethylene glycol was removed from the solution by dialyzing against water for 12 hours, and an aqueous polymeric micellar solution containing cyclosporine A was obtained.

(3) Sterilization and Drying

The dialyzed aqueous solution obtained from the step (2) above was filtered through a membrane filter, with a pore size of 0.22 μm, to sterilize it, and then freeze-dried in an aseptic environment. The average micelle size was 50 nm, and cyclosporine A in the micelle was 4.8% (loading efficiency=96%) by weight based on the total weight of the drug and the block copolymer.

Example 9

Polymeric Micelles of mPEG-PLA Containing Paclitaxel

A polymeric micellar composition containing paclitaxel was prepared by the method described in Example 7 using the following ingredients:

| | |
|---|---|
| mPEG-PLA (mw: 2,000-1,800 Daltons): | 0.85 g |
| paclitaxel: | 0.15 g |
| diethoxy polyethylene glycol (mw: 600 Daltons): | 5.00 g |

Example 10

Polymeric Micelles of mPEG-PLA Containing Paclitaxel

A polymeric micellar composition containing paclitaxel was prepared by the method described in Example 8 using the following ingredients:

| | |
|---|---|
| mPEG-PLA (mw: 2,000-1,800 Daltons): | 0.85 g |
| paclitaxel: | 0.15 g |
| dimethoxy polyethylene glycol (mw: 600 Daltons): | 4.00 g |
| ethanol: | 1.00 g |

Example 11

Polymeric Micelles of mPEG-PLA Containing Paclitaxel

A polymeric micellar composition containing paclitaxel was prepared by the method described in Example 7 using the following ingredients:

| | |
|---|---|
| mPEG-PLA (mw: 2,000-1,800 Daltons): | 0.98 g |
| paclitaxel: | 0.02 g |
| dimethoxy polyethylene glycol (mw: 300 Daltons): | 4.00 g |

Example 12

Polymeric Micelles of mPEG-PLA Containing Paclitaxel

A polymeric micellar composition containing paclitaxel was prepared by the method described in Example 7 using the following ingredients:

| | |
|---|---|
| mPEG-PLA (mw: 2,000-1,800 Daltons): | 0.95 g |
| paclitaxel: | 0.05 g |
| diacetyloxy polyethylene glycol (mw: 300 Daltons): | 4.00 g |

Example 13

Polymeric Micelles of mPEG-PLA Containing Paclitaxel

A polymeric micellar composition containing paclitaxel was prepared by the method described in Example 7 using the following ingredients:

| | |
|---|---|
| mPEG-PLA (mw: 2,000-1,800 Daltons): | 0.80 g |
| paclitaxel: | 0.10 g |
| polyethylene glycol (mw: 200 Daltons): | 5.00 g |

Example 14

Polymeric Micelles of mPEG-PLA Containing Cyclosporine A

A polymeric micellar composition containing cyclosporine A was prepared by the method described in Example 8 using the following ingredients:

| | |
|---|---|
| mPEG-PLA (mw: 2,000-1,800 Daltons): | 0.90 g |
| cyclosporine A: | 0.10 g |
| dimethoxy polyethylene glycol (mw: 200 Daltons): | 3.60 g |
| acetic acid: | 0.40 g |

Example 15

Polymeric Micelles of mPEG-PLDO Containing Testosterone

A polymeric micellar composition containing testosterone was prepared by the method described in Example 7 using the following ingredients:

| | |
|---|---|
| mPEG-PLDO (mw: 2,000-1,800 Daltons): | 0.95 g |
| testosterone: | 0.05 g |
| polyethylene glycol (mw: 600 Daltons): | 2.00 g |

Example 16

Polymeric Micelles of mPEG-PLDO Containing Doxorubicin

A polymeric micellar composition containing doxorubicin was prepared by the method described in Example 7 using the following ingredients:

| | |
|---|---|
| mPEG-PLDO (mw: 2,000-1,800 Daltons): | 0.90 g |
| doxorubicin: | 0.10 g |
| polyethylene glycol (mw: 600 Daltons): | 2.00 g |

Example 17

Polymeric Micelles of mPEG-PCL Containing a Prostaglandin

A polymeric micellar composition containing a prostaglandin was prepared by the method described in Example 8 using the following ingredients:

| | |
|---|---|
| mPEG-PCL (mw: 2,000-1,800 Daltons): | 0.95 g |
| prostaglandin: | 0.05 g |
| polyethylene glycol (mw: 600 Daltons): | 3.50 g |
| ethanol: | 0.50 g |

The particle size and drug loading efficiency of the polymeric micelles obtained in Examples 7 to 17 and Comparative Example 2 are set forth in the following Table 1.

TABLE 1

| | Drug | Content[a] (wt %) | Loading efficiency[b] | Particle size[c] (nm) |
|---|---|---|---|---|
| Example 7 | Paclitaxel | 9.8 | 98 | 45 |
| Comparative Example 2 | Paclitaxel | 8.7 | 87 | 50 |
| Example 8 | Cyclosporine A | 4.8 | 96 | 50 |
| Example 9 | Paclitaxel | 14.1 | 94 | 50 |
| Example 10 | Paclitaxel | 14.3 | 95 | 40 |
| Example 11 | Paclitaxel | 1.98 | 99 | 45 |
| Example 12 | Paclitaxel | 4.9 | 98 | 45 |
| Example 13 | Paclitaxel | 18.8 | 94 | 50 |
| Example 14 | Cyclosporine A | 9.6 | 96 | 45 |
| Example 15 | Testosterone | 4.8 | 96 | 45 |
| Example 16 | Doxorubicin | 9.7 | 97 | 40 |
| Example 17 | Prostaglandin | 4.7 | 94 | 45 |

[a] Content = Drug (g)/[Polymer (g) + Drug (g)] × 100
[b] Loading efficiency = Loading amount (g)/Initial amount (g) × 100
[c] Particle size: Size of polymeric micelle containing drug It is to be understood that the above examples are illustrative of application of the principles of the present invention. Numerous modifications and alternative arrangements can be devised without departing from the spirit and scope of the present invention. The present invention has been described above in connection with the exemplary embodiments(s) of the invention. It will be apparent to those of ordinary skill in the art that numerous modifications can be made without departing from the principles and concepts of the invention as set forth in the claims.

What is claimed is:

1. A method for preparing a biodegradable polymeric micellar composition comprising the steps of:
   1) mixing 5 to 95 wt % of a composition consisting essentially of an amphiphilic block copolymer comprising a hydrophilic poly(alkylene glycol) A block and a hydrophobic polymer B block component and 5 to 95 wt % of a phase separation medium consisting essentially of liquid poly(ethylene glycol) and optionally from 0.1 to 10 wt % water, wherein the hydrophobic biodegradable polymer B block component is a member selected from the group consisting of polylactides, polycaprolactone, copolymers of lactide and glycolide, copolymers of lactide and caprolactone, copolymers of lactide and 1,4-dioxan-2-one, polyorthoesters, polyanhydrides, polyphosphazines, poly(amino acid)s and polycarbonates, and heating the resulting mixture until said block copolymer is dissolved in said liquid poly(ethylene glycol);
   2) cooling said solution causing said block copolymer to separate from said phase separation medium thereby causing polymeric micelles formation in said solution by phase separation;
   3) dialyzing said solution against an excess of water or an aqueous solution to remove the phase separation medium; and
   4) freeze-drying said dialyzed aqueous solution thereby forming a polymeric micellar composition in a powdered state.

2. The method of claim 1, wherein said phase separation medium is a member selected from the group consisting of dihydroxy polyethylene glycol, dialkoxy polyethylene glycol and diacyloxy polyethylene glycol having a molecular weight within the range of 200 to 10,000 Daltons and a melting temperature of less than 65° C.

3. The method of claim 1, wherein said phase separation medium further comprises 0.1 to 10 wt % water.

4. A method for preparing a biodegradable polymeric micellar composition which contains a hydrophobic drug, comprising the steps of:
   1) mixing a hydrophobic drug and a composition consisting essentially of an amphiphilic block copolymer having a hydrophilic poly(alkylene glycol) A block component and hydrophobic biodegradable polymer B block component and a phase separation medium consisting essentially of liquid poly(ethylene glycol) and optionally 0.1 to 10% by weight water and optionally 0.1 to 20% by weight, based on the total weight of the drug and the block copolymer, a stabilizing compound selected from the group consisting of mannitol, sorbitol, sucrose and lactose, wherein the hydrophobic biodegradable polymer B block component is a member selected from the group consisting of polylactides, polycaprolactone, copolymers of lactide and glycolide, copolymers of lactide and caprolactone, copolymers of lactide and 1,4-dioxan-2-one, polyorthoesters, polyanhydrides, polyphosphazines, poly(amino acid)s and polycarbonates, and then heating the resulting mixture until said block copolymer is dissolved in said liquid poly(ethylene glycol), wherein said amphiphilic block copolymer in the mixture is 1 to 50% by weight, and said hydrophobic drug is 0.1 to 20% by weight, based on the total weight of the drug and the block copolymer;
   2) cooling said solution causing said block copolymer to separate from said poly(ethylene glycol) as polymeric micelles by phase separation;
   3) dialyzing said solution against an excess of water or an aqueous solution to remove the liquid polyethylene glycol; and
   4) freeze-drying said dialyzed aqueous solution thereby forming a polymeric micellar composition in a powdered state.

5. The method of claim 4, wherein said liquid polyethylene glycol is a member selected from the group consisting of dihydroxy polyethylene glycol, dialkoxy polyethylene glycol and diacyloxy polyethylene glycol and has a molecular weight of 200 to 10,000 Daltons and a melting temperature of less than 65° C.

6. The method of claim 4, wherein distilled water is added to said phase separation medium in an amount of 0.1 to 10% by weight to facilitate the phase separation.

7. The method of claim 4, wherein said hydrophobic drug is selected from the group consisting of paclitaxel, cyclosporine, prostaglandin, doxorubicin, testosterone, cisplatin and camptothecin.

8. The method of claim 4, wherein a stabilizing compound selected from the group consisting of mannitol, sorbitol, sucrose, and lactose is added to the mixture of step 1, in an amount of 0.1 to 20% by weight based on the total weight of the drug and the block copolymer.

* * * * *